(12) United States Patent
Willis

(10) Patent No.: US 12,285,616 B2
(45) Date of Patent: *Apr. 29, 2025

(54) SYSTEMS, DEVICES, AND METHODS FOR ELECTROMECHANICAL SENSING AND MAPPING

(71) Applicant: EBR Systems, Inc., Sunnyvale, CA (US)

(72) Inventor: N. Parker Willis, Atherton, CA (US)

(73) Assignee: EBR SYSTEMS, INC., Sunnyvale, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 17/863,735

(22) Filed: Jul. 13, 2022

(65) Prior Publication Data

US 2022/0347482 A1 Nov. 3, 2022
US 2024/0139523 A9 May 2, 2024

Related U.S. Application Data

(63) Continuation of application No. 16/637,130, filed as application No. PCT/US2018/044858 on Aug. 1, 2018, now Pat. No. 11,433,243.

(Continued)

(51) Int. Cl.
*A61N 1/365* (2006.01)
*A61N 1/02* (2006.01)
(Continued)

(52) U.S. Cl.
CPC ......... *A61N 1/36578* (2013.01); *A61N 1/025* (2013.01); *A61N 1/37217* (2013.01);
(Continued)

(58) Field of Classification Search
CPC ............... A61N 1/36578; A61N 1/025; A61N 1/37217; A61N 1/36507; A61N 1/378;
(Continued)

(56) References Cited

U.S. PATENT DOCUMENTS 6,798,716 B1 9/2004 Charych
7,606,621 B2 10/2009 Brisken et al.
(Continued)

FOREIGN PATENT DOCUMENTS

WO WO2007149936 12/2007
WO WO2019032350 2/2019

OTHER PUBLICATIONS

Extended European Search Report mailed Mar. 19, 2021 in European Patent Application No. 18843742.0, 7 pages.
(Continued)

*Primary Examiner* — Brian T Gedeon
(74) *Attorney, Agent, or Firm* — Perkins Cole LLP

(57) ABSTRACT

Systems, devices, and methods for tracking and determining the motion of a cardiac implant is disclosed. The motion of the implant is determined by transmitting acoustic energy to a tissue location using an acoustic controller-transmitter comprising an array of acoustic transducers; wherein the implant is configured to convert the transmitted acoustic energy to electrical energy; and the tracking is achieved by determining the electrical energy delivered to the tissue throughout one or more cardiac cycles in order to create a motion profile of the cardiac implant.

23 Claims, 11 Drawing Sheets

Related U.S. Application Data

(60) Provisional application No. 62/542,741, filed on Aug. 8, 2017.

(51) Int. Cl.
    *A61N 1/372*     (2006.01)
    *A61B 5/00*      (2006.01)
    *A61B 5/11*      (2006.01)
    *A61B 5/35*      (2021.01)

(52) U.S. Cl.
    CPC .......... *A61B 5/1102* (2013.01); *A61B 5/1126* (2013.01); *A61B 5/35* (2021.01); *A61B 5/7278* (2013.01)

(58) Field of Classification Search
    CPC ... A61N 1/3787; A61B 5/1102; A61B 5/1126; A61B 5/35; A61B 5/7278; A61B 5/282; A61B 5/287; A61B 2560/0219; A61B 5/1107; A61B 5/061; A61B 5/076
See application file for complete search history.

(56) References Cited

U.S. PATENT DOCUMENTS

| | | | |
|---|---|---|---|
| 9,907,968 | B2 | 3/2018 | Moore et al. |
| 9,968,787 | B2* | 5/2018 | Kane ................. A61B 5/1118 |
| 10,080,903 | B2 | 9/2018 | Willis et al. |
| 2008/0058656 | A1 | 3/2008 | Costell et al. |
| 2009/0265128 | A1 | 10/2009 | Markowitz et al. |
| 2011/0319779 | A1 | 12/2011 | Sweeney et al. |
| 2012/0093281 | A1 | 4/2012 | Zamyatin et al. |
| 2013/0218251 | A1 | 8/2013 | Penner |
| 2014/0094891 | A1 | 4/2014 | Pare et al. |
| 2014/0200457 | A1 | 7/2014 | Shuros et al. |
| 2014/0207210 | A1 | 7/2014 | Willis et al. |
| 2017/0056649 | A1* | 3/2017 | Kane ................. A61N 1/3756 |

OTHER PUBLICATIONS

International Search Report and Written Opinion mailed Oct. 11, 2018 for PCT/US2018/044858, 11 pages.

\* cited by examiner

SYSTEMS, DEVICES, AND METHODS FOR ELECTROMECHANICAL SENSING AND MAPPING

CROSS-REFERENCES TO RELATED APPLICATIONS

This application is a continuation of U.S. patent application Ser. No. 16/637,130, titled "SYSTEMS, DEVICES, AND METHODS FOR ELECTROMECHANICAL SENSING AND MAPPING", filed Feb. 6, 20202, which is a U.S. National Phase Application under 35 U.S.C. § 371 of International Application No. PCT/US18/44858, titled "SYSTEMS, DEVICES, AND METHODS FOR ELECTROMECHANICAL SENSING AND MAPPING", filed Aug. 1, 2018, which claims the benefit and priority of U.S. Provisional Patent Application No. 62/542,741, titled "SYSTEMS, DEVICES, AND METHODS FOR ELECTROMECHANICAL SENSING AND MAPPING", filed on Aug. 8, 2017, the full disclosure of each of which is incorporated herein by reference.

BACKGROUND OF THE INVENTION

The systems, devices, and methods of this disclosure relates to electromechanical mapping and sensing the motion of the heart and other body organs and tissues by means of one or more implantable devices.

A single cycle of cardiac activity may be divided into the diastole phase and the systole phase. The diastole phase is a period of time when the ventricles are relaxed and not contracting. Throughout most of this period, blood is flowing from the left atrium (LA) and right atrium (RA) into the left ventricle (LV) and right ventricle (RV). The systole phase is a period during which the left and right ventricles contract and eject blood into the aorta and pulmonary artery, respectively. During the systole phase, the aortic and pulmonic valves open to permit ejection into the aorta and pulmonary artery. The atrioventricular valves are closed during systole, therefore no blood is entering the ventricles. However, blood continues to enter the atria though the vena cavae and pulmonary veins.

Furthermore, changes in aortic pressure (AP), left ventricular pressure (LVP), left atrial pressure (LAP), left ventricular volume (LV Vol), and heart sounds during a single cycle of cardiac contraction and relaxation may be related in time to the electrocardiogram.

Mechanical motion data from various imaging modalities, e.g. MRI and echocardiography may be used in cardiac resynchronization therapy (CRT). In some cases, algorithms may be applied to MRI data to predict the best pacing location as the site that is the most mechanically delayed. Investigators have also used various motion metrics primarily based on echo strain studies to determine the effectiveness of CRT therapy.

Thus it would be desirable to construct a mechanical motion profile and to utilize the mechanical motion profile to determine the pacing time window and/or pacing location.

BRIEF SUMMARY OF THE INVENTION

The embodiments herein describe aspects of devices, systems, and methods that are configured to track the location of an implantable receiver-stimulator in the heart relative to the controller-transmitter to produce a 3D motion sensing or mapping of the receiver-stimulator. In one aspect, an electrical location signal generated by the receiver-stimulator is used to locate the receiver-stimulator. By applying the location signal tracking continuously throughout one or more cardiac cycles, one aspect of the system is configured to dynamically track the 3D motion of the receiver-stimulator to create a motion profile. In another aspect, optionally, the 3D motion of the receiver-stimulator could be combined with the EKG data wherein the EKG data may be used to normalize the motion profile. In yet another aspect, the 3D motion of the receiver-stimulator may be correlated with EGM data obtain at a one or more locations of the heart to provide a electromechanical motion profile of a tissue region, such as a potential implant site.

In one embodiment, the system is configured to utilize the electromechanical mapping data to determine the general locations of the receiver-stimulator at the end of diastole (ventricles full of blood) and/or the end of systole (ventricles emptied). In one aspect, the system is configured to trigger pacing upon the determination of the electrode location at the end diastolic position. In another aspect, the system is configured to deliver the pacing pulse immediately or delayed by a fixed time amount. In yet another aspect, the delivery of the pacing pulse could by contingent on the receiver-stimulator remaining in the end diastolic location for a fixed time period. Detection of a departure from the end diastolic location of the electrode would inhibit pacing. Lack of motion from end-diastolic location for a fixed duration would imply that the ventricles are fully relaxed, filled with blood, therefore it is appropriate to deliver a pacing pulse. In another aspect, the system may be configured to initiate the stimulation prior to the end of diastolic position such that the system accounts for the electro-mechanical delay of the pacing pulse.

This and other aspects of the present disclosure are described herein.

BRIEF DESCRIPTION OF DRAWINGS

Present embodiments have other advantages and features which will be more readily apparent from the following detailed description and the appended claims, when taken in conjunction with the accompanying drawings, in which:

DETAILED DESCRIPTION OF THE INVENTION

Figure 1:
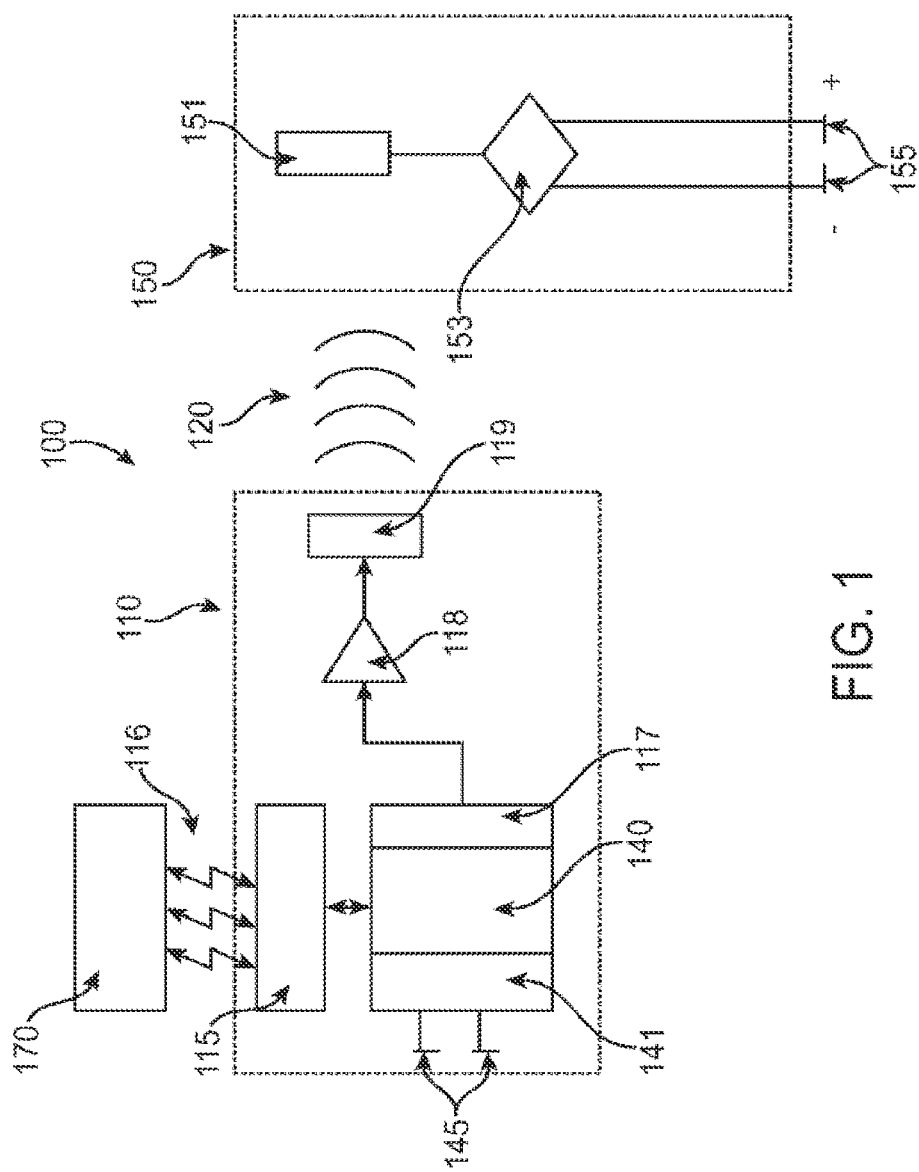
FIG. 1 is a block diagram illustrating a tissue stimulation system.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Various embodiments are described herein with reference to the figures. The figures are not drawn to scale and are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and may be practiced in any other embodiments even if not so illustrated.

Systems, devices, and methods to provide electromechanical motion sensing and/or mapping of the heart are disclosed. In one aspect, the motion and/or mapping data is used to optimize the timing and location for tissue stimulation. More specifically, aspects of systems, devices, and methods for motion sensing and mapping the local physiological values, sensing the motion, and/or the shape of the heart to determine the activation profile of the heart and, preferably, to analyze the resulting maps to determine possible optimizations in the activation profile for stimulation of the tissue.

In one embodiment, the system comprises a first implanted device, generally referred to as the controller-transmitter or acoustic controller-transmitter, which provides appropriate timing and control functions and transmits acoustic energy to a second implanted device. The second implanted device, generally referred to as the receiver-stimulator, receives the acoustic energy and converts it into electrical energy and applies that electrical energy to electrodes. The second device is adapted to be permanently implanted at a location where it is desired to provide electrical stimulus, with at least one electrode in direct contact with the cardiac muscle or other body tissue, Optionally, two or more receiver-stimulators may be implanted to be controlled by a single controller-transmitter.

In one aspect, the system is configured to track the location of one or more of the receiver-stimulators relative to the acoustic source such as the controller-transmitter to sense the motion and to produce a motion profile. In another aspect, wherein the receiver-stimulator is implanted or otherwise connected to the heart. In one aspect, an electrical location signal generated by the receiver-stimulator is used to locate the receiver-stimulator. In an embodiment, the receiver-stimulator generates the electrical location signal in response to receiving acoustic energy from the controller-generator. By applying the location signal tracking periodically or continuously throughout one or more cardiac cycles, one aspect of the system is configured to dynamically track the 3D motion of the receiver-stimulator to create a motion profile of the receiver-stimulator. In another aspect, the 3D motion of the receiver-stimulator could be combined with the EGM data to provide complete electromechanical mapping data of a tissue region, such as a potential implant site.

In one embodiment, the system is configured to utilize the mechanical motion data to determine the general locations of the receiver-stimulator at any point of the diastolic or systolic phases and in particular at the end of diastole (ventricles full of blood) and/or the end of systole (ventricles emptied). In one aspect, the mechanical motion data may be first normalized with EKG data to establish locations of the receiver-stimulator during systole and diastole. In one embodiment, the system may learn the time it takes to fill from end systole to end diastole. The system may then use the learned fill time to as a reference to determine the appropriate timing for pacing. In one embodiment, after the initial normalization, no further EKG data are used and the motion of the heart is established with the sensed mechanical motion data. In another embodiment, EKG data may be continuously applied to calibrate the mechanical motion data. In various embodiments, EKG data may be collected using surface EKG electrodes. Additionally or alternatively, EKG data may be collected using sensing electrodes mounted on the controller-transmitter or the delivery system.

In one aspect, the system is configured to trigger pacing upon the determination of the electrode at the end diastolic position. In another aspect, once the mechanical motion data is established, the system may be configured to deliver the pacing pulse to optimize energy delivery. In one aspect, immediately or delayed by a fixed time amount. In yet another aspect, the delivery of the pacing pulse could by contingent on the receiver-stimulator remaining in the end diastolic location for a fixed time period. Detection of a departure from the end diastolic location of the electrode would inhibit pacing. Lack of motion from end-diastolic location for a fixed duration would imply that the ventricles are fully relaxed, filled with blood, therefore it is appropriate to deliver a pacing pulse. In yet another aspect, the delivery of the pacing pulse may by contingent on the receiver-stimulator being in a desired location within the systolic-diastolic motion cycle thus anticipating the end of diastole to synchronize the pacing pace to an optimum point in the electro-mechanical cycle. In an embodiment, the system is configured to initiate the stimulation prior to the end of diastolic position such that the system accounts for the electro-mechanical delay of the pacing pulse.

In another aspect, the mechanical motion data of the receiver-stimulator may be correlated with EGM data and/or electrogram characteristics to create an electromechanical motion profile. In one embodiment, the electromechanical motion profile may be utilized to determine an abnormal activation profile due to a conduction abnormality, such as a block, for assessing the effects of tachycardia or for assessing changes in the activation profile as a function of heart rate. In yet another embodiment, the 3D motion of the receiver-stimulator alone, or correlated with geometrical characteristics of the heart or with EGM data or electrogram characteristics may be utilized to compare the local activation time to the movement of a segment of the heart. For example, the activation time of the segment to movement of the segment relative to the movement of surrounding segments.

For example, the mechanical motion data, alone or in combination with additional data may be used to determine the geometry and/or changes in the geometry of at least a portion of the heart as a function of time and/or phase of the cardiac cycle. For example, the existence of a ventricular dyssynchrony or electrical-mechanical dissociation may be determined from characteristics during systole. Likewise, a dilated ventricle may be determined from the determined volume.

In one embodiment, the system is configured to track the location of the receiver-stimulator relative to the controller-transmitter over one or more cardiac cycle by using a location signal and/or a locator signal as disclosed in U.S. application Ser. No. 14/221,040, herein incorporated by reference. It should be noted that the location signal tracking embodiments as described are just examples of how to determine the 3D motion of the receiver-stimulator to establish a motion profile of the tissue area.

More specifically, in one embodiment, the system is configured to use an array of acoustic transducers of the controller-transmitter to transmit acoustic energy at a specific location in the body. The acoustic receiver of the receiver-stimulator is configured to generate an electric location signal via one or more electrodes, whenever it receives acoustic energy. Separate detection electrodes may detect the electric location signal indicating when the array of acoustic transducers is focused on the acoustic receiver and revealing the location of the receiver. The transducer array could be configured to sequentially steer the acoustic energy until the location signal is detected or a preset time limit has been reached. The location signal could be detected by a sensing circuit on the controller-transmitter.

In another embodiment of the invention, the controller-transmitter would be further configured to adjust the transducer array to transmit focused acoustic energy to the region of the tissue associated with detecting the location signal. This focused energy could be adequate to stimulate tissue and, in particular, cardiac tissue. In yet another embodiment, this focused energy would be generated based on characteristics of the location signal.

In yet another embodiment of this invention, an implantable acoustic controller-transmitter comprises an adjustable transducer array configured to transmit acoustic energy into tissue; an implantable acoustic receiver-stimulator comprises a transducer assembly adapted to receive the acoustic energy and convert the acoustic energy to electrical energy, where the transmitter is configured to transmit an acoustic locator signal towards the receiver, and the receiver is configured to generate a location signal. Optionally, the location signal could be either an electrical output or an acoustic transmission in response to the locator signal.

Referring now to FIG. 1, where one embodiment of a leadless tissue stimulation system is shown as system 100. An implantable or external controller-transmitter module 110 generates acoustic waves 120 of sufficient amplitude and frequency and for a duration and period such that the receiver-stimulator module 150 electrically stimulates tissue. An external programmer 170 wirelessly communicates with an implantable controller-transmitter module 110, typically by radio frequency telemetry means 116, to adjust operating parameters. The implantable controller-transmitter module 110 comprises a telemetry receiver 115 for adjusting the transmit acoustic characteristics, control circuitry 140 and signal generator 117, a power amplifier 118, and an output transducer assembly 119 for generating the acoustic beam 120 transmitted to receiver-stimulator 150. Understandably, the controller-transmitter 110 transfers acoustic energy to the receiver-stimulator 150 leadlessly. Control circuitry 140 contains an electrical signal sensing circuit element 141 connected to one or more sensing electrodes 145 disposed on the outer casing of the controller-transmitter or connected via cables to the controller-transmitter. Alternatively, electrical sensing circuit 141 may be a typical electrogram sensing circuit or may be an electrical spike detection circuit. Additionally, controller-transmitter 110 may be configured to collect and process EKG data collected using sensing electrodes 145.

The receiver-stimulator 150 comprises a piezoelectric receiving transducer 151, rectifier circuitry 153, and at least one tissue contacting electrode 155. In this embodiment, acoustic energy received and rectified by the receiver-stimulator is directly applied to the electrodes 155. Alternatively, the receiver-stimulator module 150 may comprise multiple transducer/rectifier channels in a variety of combinations, which may be in series or parallel orientations, or the construction may perform impedance matching, and/or for signal filtering to increase the efficiency of the receiver-stimulator, as disclosed in co-pending U.S. application Ser. No. 11/315,524, herein incorporated by reference.

Figure 2A:
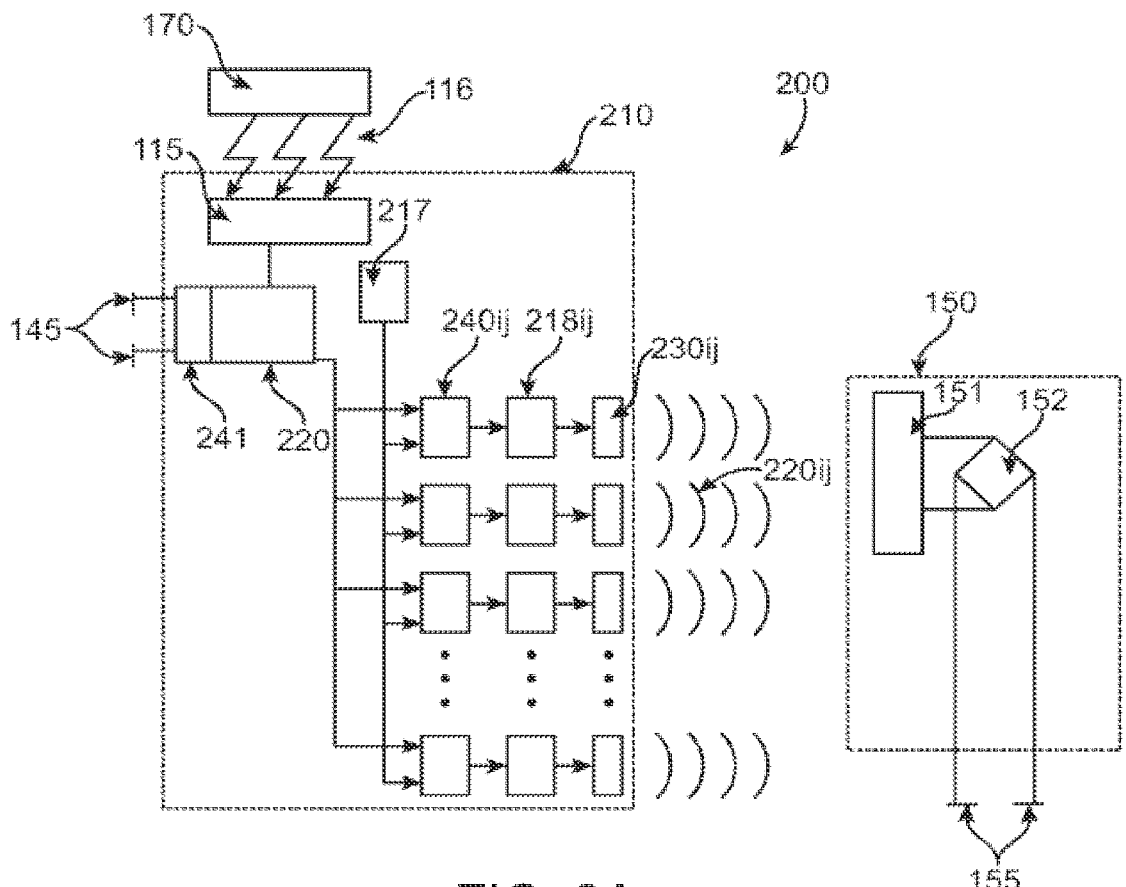
FIGS. 2A-B illustrate one embodiment of this invention.

Referring now to FIG. 2A, where one embodiment of the present invention is shown as system 200. The controller-transmitter module 210 is placed either inside the body, but remote from myocardial tissue, or outside the body in contact with the body surface. The external programmer 170 communicates with the controller-transmitter module 210, typically by radio frequency telemetry 116. The telemetry module 115 inside the controller-transmitter unit 210 provides two-way communications directly with the control circuitry 220. A separate continuous wave (CW) signal generator 217 inside the controller-transmitter 210 provides the acoustic operating frequency for the system.

Figure 2B:
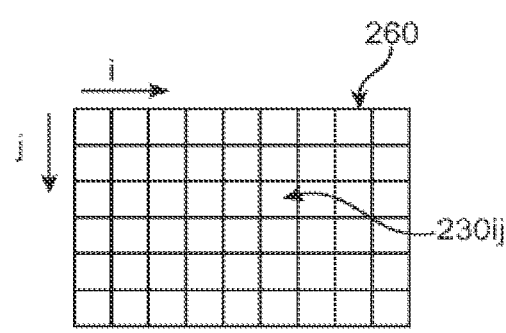

The control circuitry 220 and signal generator 217 are both connected to each channel of a two dimensional acoustic transducer array 260 (shown in FIG. 2B), where each channel comprises a transmit/receive transducer element 230 $ij$, a power amplifier 218 $ij$ and phase shifter module 240 $ij$. The phase shifter module 240 $ij$, ensures that during acoustic transmissions, each channel transmits with the correct phase so as to form an efficient, focused narrow acoustic beam intended to precisely intercept the receiver-stimulator. A control signal from control circuitry 220 defines the transmit phases. The output of the phase shifter 240 $ij$ then passes to the power amplifier 218 $ij$ of the channel, which is also under the control of the control circuitry 220, and which may be either in an OFF state, a full ON state, or at selected levels of intermediate power which might be required for beam shading. The output of the power amplifier passes directly to the channel transducer element 230 $ij$. One embodiment of using the phase shifter for each output channel has been described above. Other techniques may also be employed, such as direct formatting of the transmit beam by the control circuitry 220.

The controller-transmitter 210 would scan a spatial region by sending narrow acoustic beams (the locator signals), looking for a response (the location signal), from the receiver-stimulator. If the focused, directed acoustic beam intersects the receiver-stimulator the acoustic energy is converted by the receiver-stimulator and delivered as an electrical output onto the electrodes 155. This electrical output would generate an electrical signal that would be detected by sensing electrodes 145 and detection circuits 241 of the controller-transmitter 210. If the controller-transmitter 210 does not detect an electrical signal within a reasonable time frame, the inference would be that the directed acoustic beam did not intersect the receiver-stimulator and the directed acoustic beam was "off target." Such time frames may be predetermined or determined based on location signal characteristics. Then, the controller-transmitter 210 adjusts the focused, directed beam to another portion of the region where the receiver-stimulator 150 may be located, possibly chosen to be close to the previous region, and repeat the locator signal transmission thereby scanning the spatial region iteratively. In this manner, an electrical signal is generated and detected if the receiver-stimulator 150 is in the spatial region being scanned. The controller-transmitter 210 then uses the focused, directed beam parameters that resulted in a detected electrical signal (location signal) as the target (transmission region) for the efficient transmission of a narrow acoustic beam of acoustic energy towards the receiver-stimulator. Alternatively, the controller-transmitter 210 could then analyze characteristics of the detected electrical signal to determine whether the directed transmitter beam was adequately targeting the receiver-stimulator 150.

Figure 3:
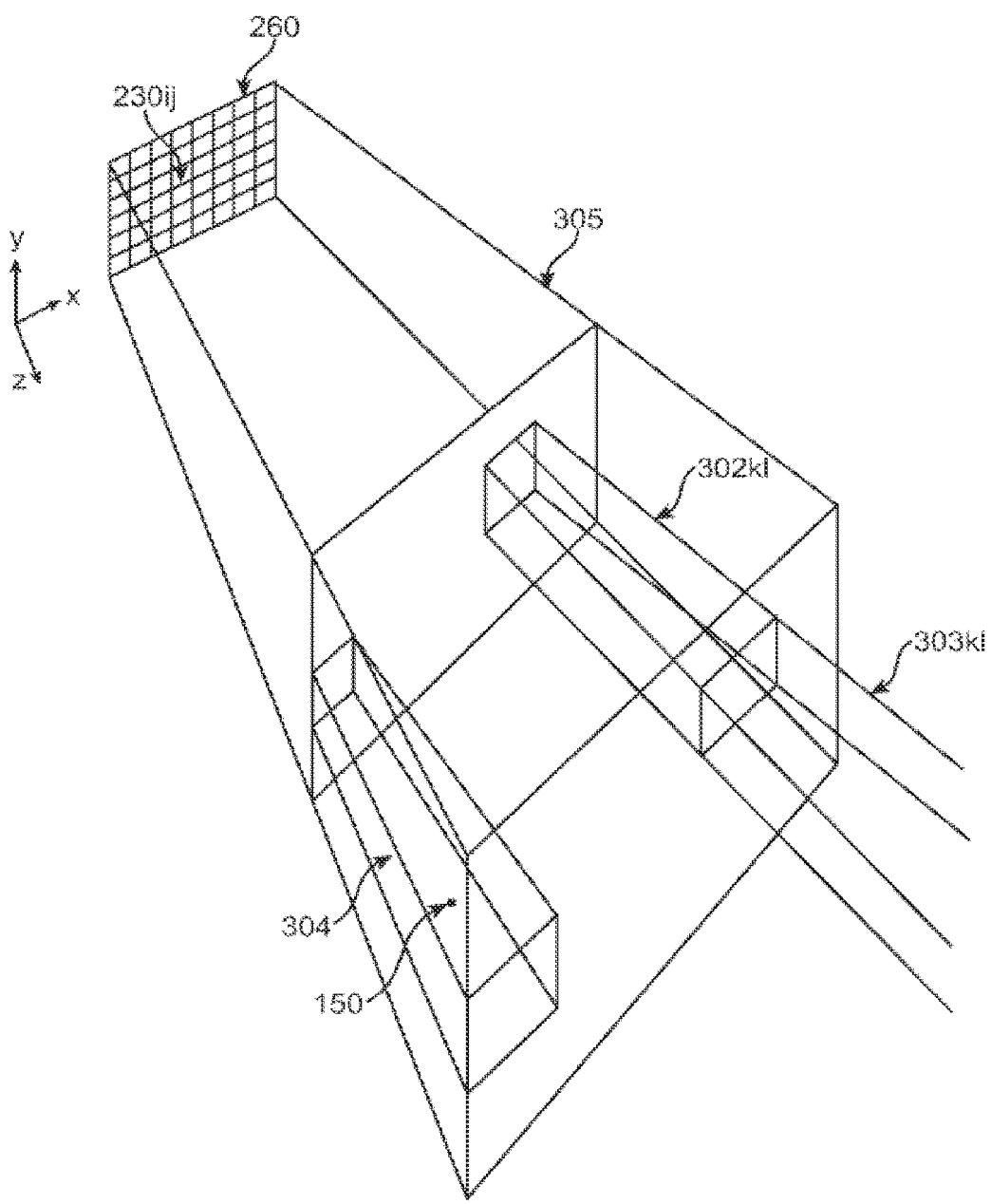
FIG. 3 illustrates the acoustic array scanning a region for location signals in response to locator signals.

The scanning process is shown in more detail in FIG. 3. The phased array 260 of the controller-transmitter 210 is composed of individual transducers 230 *ij*. For convenience the array is oriented in the x-y plane at z=0. The spatial volume to be scanned 305 encompasses all of the possible locations for the receiver-stimulator 150, and, again for convenience, is located in the z>0 half space with respect to the phased array 260. The extent of 305 is constrained by anatomical limits and may vary depending on the specific stimulation application. The spatial volume 305 is broken up into multiple volumes 302 *kl*, which are individually scanned or tested. The volumes 302 *kl* may overlap; however, it is desirable to have the entire collection of volumes cover the region 305. The array is aimed at a volume 302 *kl* by setting the appropriate phase parameters for the array elements 230 *ij*.

In one aspect, the embodiments described above may be applied continuously or periodically throughout one or more cardiac cycles to dynamically track the location of the receiver-stimulator as the mechanical motion of the heart through the cardiac cycles affects the location of the receiver-stimulator and thereby achieve 3D motion tracking of the receiver-stimulator to construct a motion profile of the receiver-stimulator. In one embodiment, the motion of the heart is determined relative to the movements of the receiver-stimulator. In another embodiment, where more than one receiver-stimulators are tracked, a map of the heart relative to the movement of the receiver-stimulators is created.

In another aspect, the 3D motion data may be captured during pacing or stimulation of the tissue. Clearly the 3D motion of the receiver-stimulator when pacing captures will be different from when it does not. Not only will the 3D motion vary, more importantly and more easily detected, the onset of the 3D motion relative to the application of the pacing pulse will change. In one aspect, the motion timing difference between the pacing state versus the non-pacing state could be used to reliably detect capture at the receiver-stimulator.

In one embodiment, the devices, systems, and methods of the present embodiments further comprises at least one computing element with at least one processing element and memory element to process the 3D motion data. In one embodiment, the computing element is configured to correlate the motion data with additional data such as geometrical characteristics of the heart, EGM data and/or electrogram characteristics such as another cardiac reference including but not limited to a co-implant.

In one embodiment, several metrics could be applied to assess a tissue region via the motion data of the receiver-stimulator, including, but not limited to: A) mechanical delay during intrinsic conduction or during right ventricular pacing; B) change/reduction in mechanical delay as a result of left ventricular pacing vs. intrinsic conduction or right ventricular pacing; C) the overall magnitude of the cardiac motion; D) volume data; and/or other characteristics of the tissue region.

In yet another aspect of the present embodiments, a receiver-stimulator is configured to be implantable in the right ventricle and/or the left ventricle endocardially and/or epicardially. In one aspect, a controller-transmitter configured to be implantable subcutaneously, exemplarily, in one embodiment, the controller-transmitter is configured to be implantable subcutaneously in the intercostal space. As previously discussed, the controller-transmitter is configured to deliver acoustic energy and the receiver-stimulator is configured to convert the acoustic energy to electrical energy where the electrical energy is delivered to the tissue to cause electrical stimulation, such as pacing stimulation.

It is noted that aspects of the present embodiments may be applied in a co-implanted configuration where the controller-transmitter and the receiver-stimulator are both implanted in the body as described above. It is also noted that aspects of the present embodiment may be applied where one or more receiver-stimulators are implanted to a tissue region or temporarily connected to the tissue region, a temporary electrical connection, such as via a delivery system may be used to determine the EGM generated by the stimulation of heart tissue is monitored using one or more temporary electrode connections on the receiver-stimulator or other electrodes, e.g., surface EKG electrodes or other electrodes mounted on the delivery system.

The temporary electrical connection may also be used to determine the efficiency of conversion of energy to electrical stimulation energy by the receiver-stimulator at a given location in the heart. In one embodiment, this is accomplished by delivering acoustic energy from a wireless controller-transmitter or similar implantable or externally-applied acoustic transmitter to the wireless receiver-stimulator, converting the acoustic energy to electrical energy, and delivering electrical energy to the heart tissue through the receiver-stimulator's cathode and an anode, while monitoring the electrical energy using an external monitor connected to the electrodes via the temporary electrical connections through the delivery system. The electrical energy in this embodiment need not be at pacing strength, since conversion efficiency may be gauged even at lower energy levels.

As described in the co-pending U.S. patent application Ser. No. 15/043,210 incorporated herein by reference, a delivery system may be configured to provide signal interconnect with an external monitor and pacing controller to facilitate location selection during an implant procedure by collecting local EGM data, performing direct electrical pacing of the heart via electrical connections to one or more of the electrodes of the receiver-stimulator device, and evaluating operational efficiency of the receiver-stimulator.

In one aspect, where EGM data may be collected, such as via a temporary electrical connection, the location of the implanted receiver-stimulator could be tracked over the course of a cardiac cycle to create a mechanical motion profile. In one aspect, EGM data is configured to be simultaneously or periodically recorded. By combining the EGM data with the mechanical motion profile to determine the general locations of the receiver-stimulator at the end diastole (ventricles full of blood), the end systole (ventricles emptied), or both. In one embodiment, the controller-transmitter is configured to trigger pacing via determination of the receiver-stimulator at the end diastolic position. In one embodiment, delivery of the pacing pulse could be immediate or delayed by a fixed time amount. In yet another embodiment, delivery of the pacing pulse could by contingent on the receiver-stimulator remaining in the end diastolic location for a fixed time period. In yet another embodiment, detection of a departure from the end diastolic location of the receiver-stimulator would inhibit pacing. Lack of motion from end-diastolic location for a fixed duration would imply that the ventricles are fully relaxed, filled with blood, therefore it is appropriate to deliver a pacing pulse.

In one aspect, the determination of the location of the receiver-stimulator may be accomplished by periodic acoustic transmission at the same location say every 1-200 ms. In some aspects, continuous tracking of the receiver-stimulator location may be performed every 1-100 ms rather than directing the spotlight to a single transmit angle. In some aspects, the system, method and device are configured to track hemodynamic loss or loss of motion due to rapid pacing based on the receiver-stimulator motion. If the receiver-stimulator moves out of this location as determined by the lack of or a decreased in electrical output as elicited by acoustic transmission, then the acoustic transmission may be adjusted to re-locate the receiver-stimulator. In one aspect, if the receiver-stimulator remains in the same location for more than a fixed programmable time interval representing a low rate limit of electrical output then deliver an electrical output as a pacing pulse. In this sense the system functions as a brady pacemaker. If the receiver-stimulator does not move after the application of the pacing pulse, then it may be conclude that the patient is in a hemodynamically unstable rhythm and an Antitachycardia pacing protocol would be applied. If there was no motion after the Antitachycardia pacing then a defibrillation shock would be delivered. This scheme could also be used in conjunction with EGM monitoring however the potential advantage of hemodynamic monitoring is that it is much faster than electrical detection used in ICDs which requires analysis of multiple beats to detect either VT or VF. A simple hemodynamic sensor has the advantage of rapid intervention at the onset of the arrhythmia which could make the Antitachycardia pacing more effective. In some aspects, the system, method and device are configured to detect electrical-mechanical dissociation or pulseless electrical activity based on EGM data and the location of one or more receiver-stimulators. For example, if organized electrical activity is detected along with a lack of or decreased motion of one or more receiver stimulators, then the system may conclude that the patient is in a state of electrical-mechanical dissociation.

In an embodiment, the system is configured to trigger pacing based on EKG data collected using sensing electrodes mounted on the controller-transmitter. In one aspect, the system initiates pacing upon detection of the initiation of QRS. Delivery of the pacing pulse could be immediate or delayed by a fixed time amount.

In various embodiments, the system may use one or more receiver-stimulators for tissue capture and pacing along with one or more additional receiver-stimulators or non-stimulating receivers for heart wall motion detection. As an example, one or more receiver-stimulators may be placed at clinically optimal pacing locations which may not necessarily correspond to the location of greatest motion potential, such as the bundle of His. Additionally, one or more receiver-stimulators may be anchored at locations with large motion, such as the lateral wall. In this way the system would achieve both optimum pacing potential and optimum motion detection. In one embodiment, the receiver used for motion detection could have the same design as the receiver-stimulator used for tissue capture. In another embodiment, the receiver used for motion detection could have a modified design since it would not be required to provide tissue capture. For example, the motion detection receiver could be smaller, have a different shape, use fewer transducers, rectifiers, or other components, or have a different electrode configuration. In one aspect the electrode of the motion detection receiver could be at the tip of an anchoring needle. In other aspects, the electrode of the motion detection receiver could be at a location configured to just touch the heart wall or on the body of the receiver.

EXAMPLES

Experimental data were gathered in a dual site experimental model implanted with two receiver-stimulators: one in the left ventricle and one in the right ventricle. Using the Test2 Command, a manufacturing test command that performs repeated transmit query pulses to a fixed target location and stores the resulting query response amplitudes which may be read back through a base station radio. The controller-transmitter delivered acoustic energy to the last known location of a given receiver-stimulator. This essentially created a pulsed acoustic "spotlight" directed at the last known location of the receiver-stimulator. It was expected to observe a periodic waveform indicating the motion of the receiver-stimulator over time as it repeatedly left the spotlight beam and then returned back to a spatial point sometime around the onset of QRS. All of this testing was performed in normal sinus rhythm.

The initial experiment directed the beam at the receiver-stimulator of the right ventricle position from several minutes in the past. One hundred points were recorded over approximately one second and the result is as shown in FIG. 4.

Figure 4:
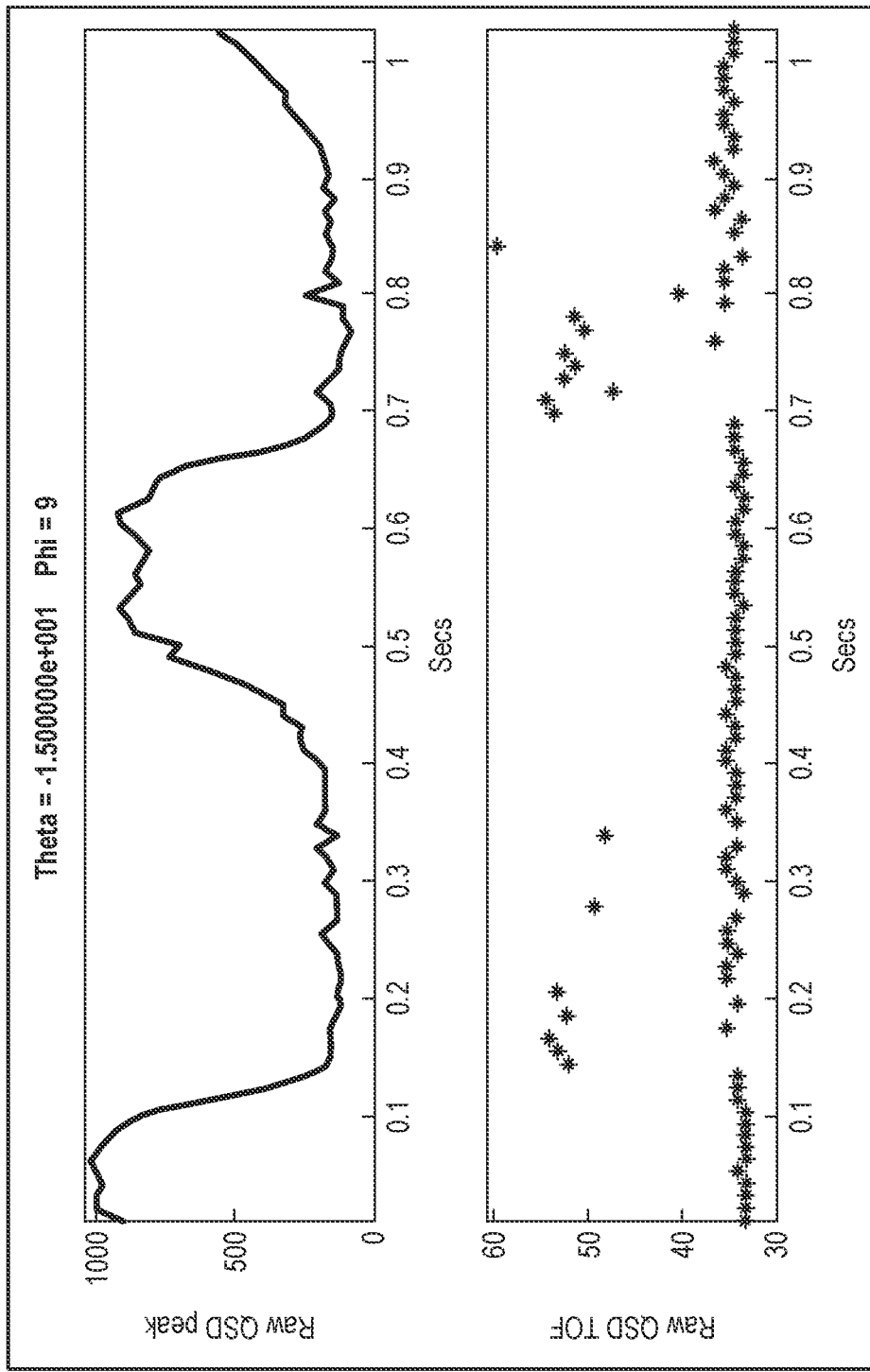
FIG. 4 illustrates sensor data where the acoustic beam is directed at the receiver-stimulator of the right ventricle.

As seen in FIG. 4, there is a clear and rapid drop in QSD amplitude after the peak at approximately 1000 uV. Assuming that the receiver-stimulator position is correct, it may be concluded that this is due to ventricular contraction, whereas the rise in QSD amplitude is due to ventricular filling during end diastole.

A similar test targeting the last known location for the receiver-stimulator of the left ventricle. The results for a five second are shown FIG. 5.

Figure 5:
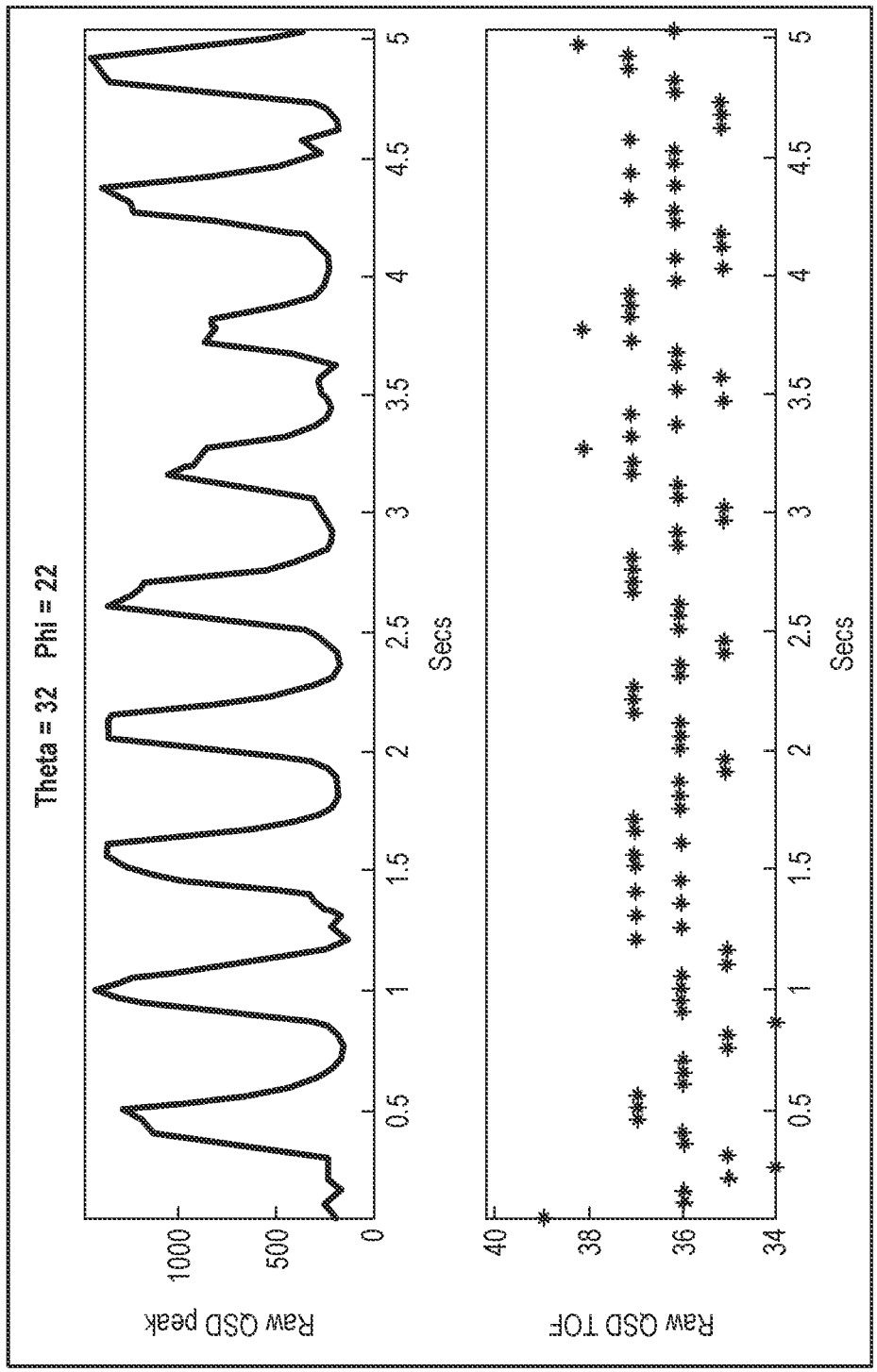
FIG. 5 illustrates sensor data where the acoustic beam is directed at the receiver-stimulator of the left ventricle.

As seen in FIG. 5, the variability in peak amplitude was likely due to respiratory variability. There is also a clear periodic variability in the time-of-flight (TOF). Variability in the right ventricle TOF was due to low amplitude QSD noise detection.

Figure 6:
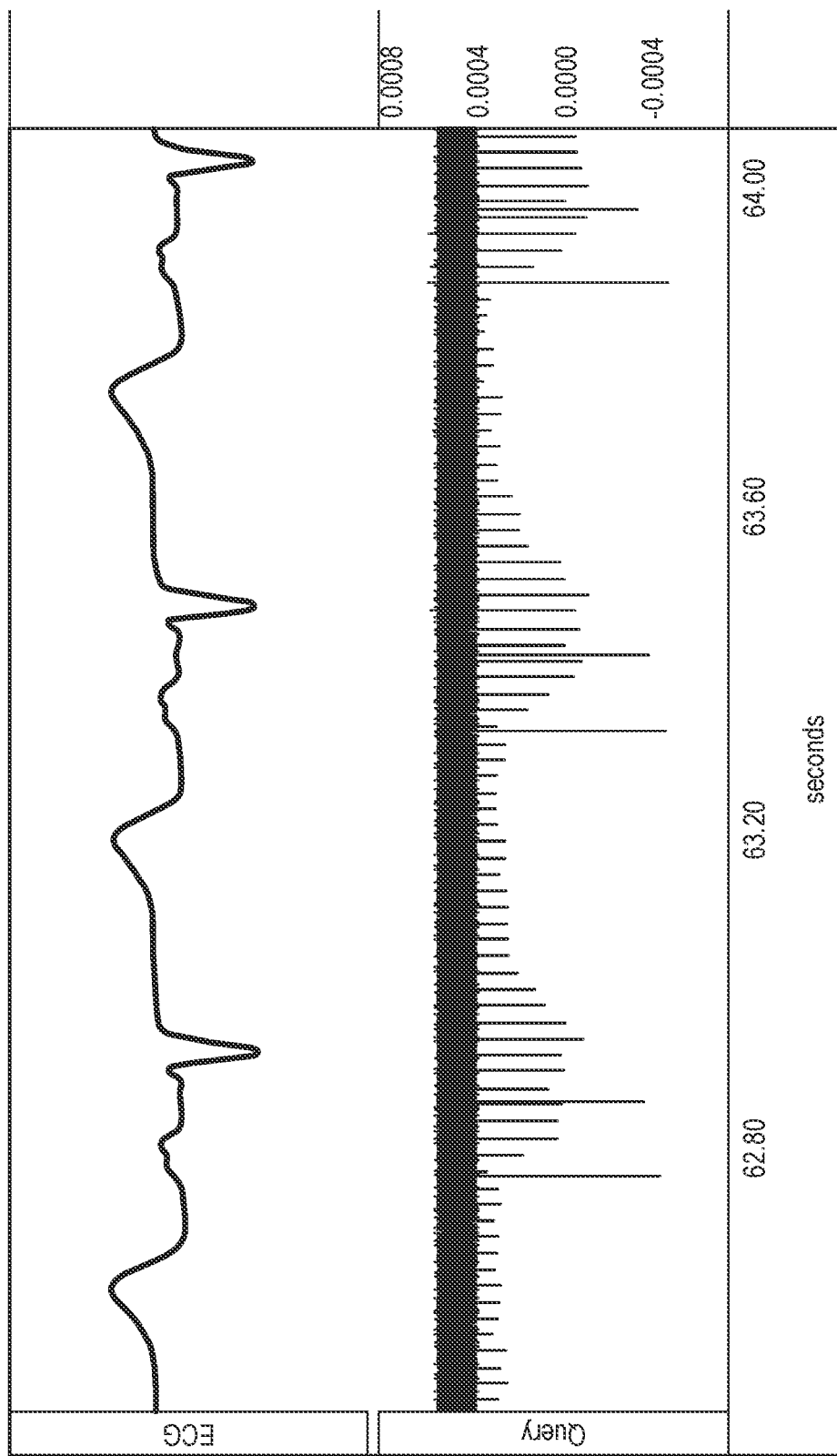
FIG. 6 illustrates a high sample rate EKG in parallel with a typical low bandwidth EKG.

Furthermore, the QSD "spot-light" waveform correlate with cardiac electrical activation by recording a high sample rate EKG in parallel with a typical low bandwidth EKG during these experiments, as shown in FIG. 6.

As seen in FIG. 6, there are clearly two additional spikes, most likely from the co-implant device. The device was in an AOO mode (there is no actual OFF mode) with the telemetry wand in place. It is likely that these were telemetry artifacts that are aligned with V, which is likely due to far field sensing of the A wave by atrial lead of the co-implant device. It may be confirmed that from the surface EKG that the high amplitude portion of the QSD waveform is associated with a full ventricle. This confirms that the last known location of the receiver-stimulator used as the direction for the "spot-light" illumination is still reasonably accurate.

Figure 7A:
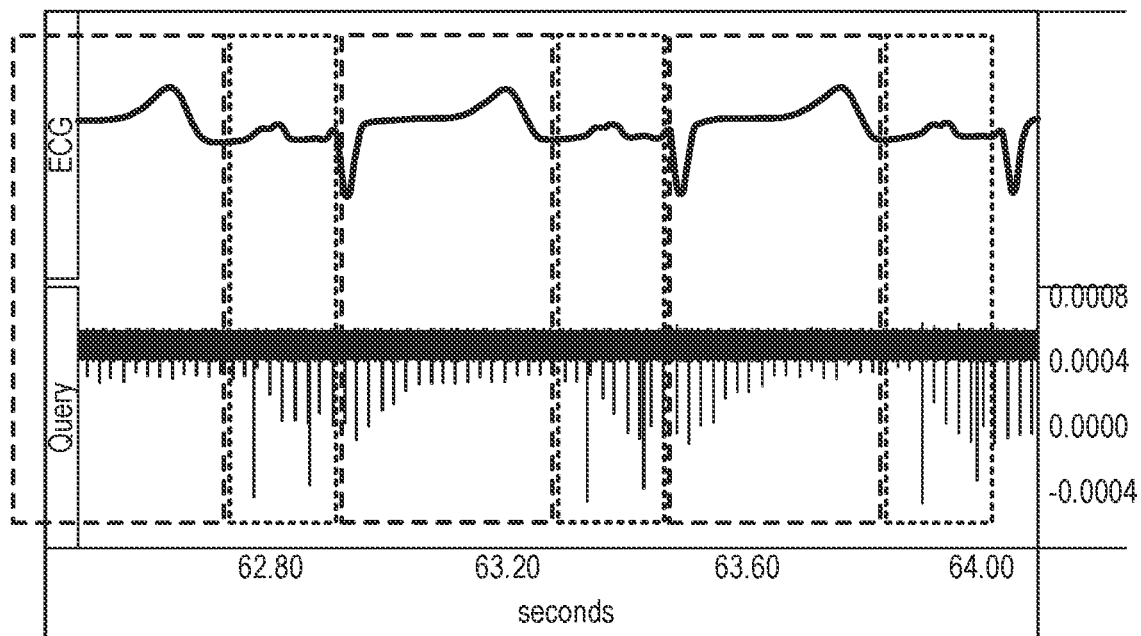
FIGS. 7A-B illustrate the cardiac cycle are shown indicating systole and diastole in relation to the electrical stimulation and motion tracking.
Figure 7B:
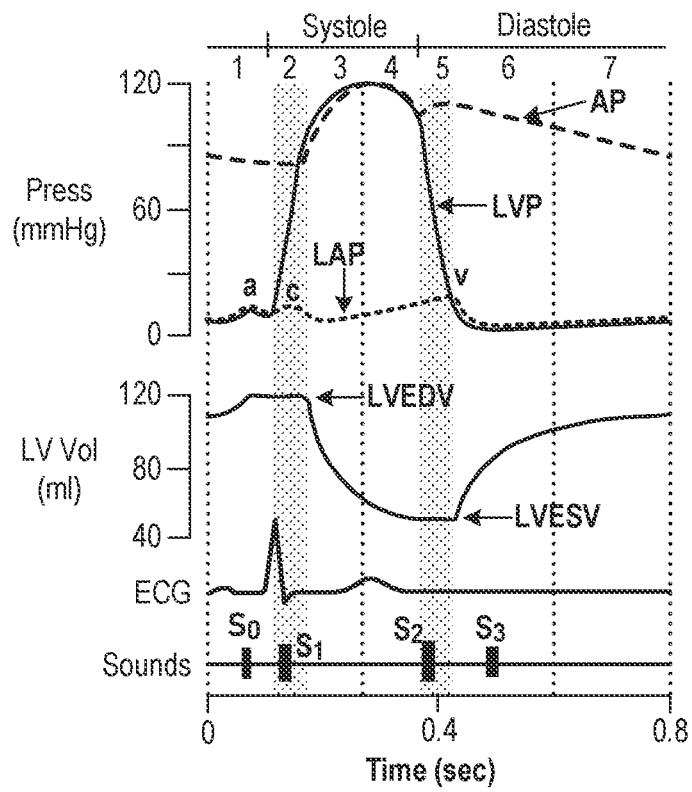

Referring now to FIGS. 7A-7B, where a graphical representation of the cardiac cycle is shown indicating systole and diastole. It is noted that the time of the peak QSD response is associated with both the end of diastole and beginning of systole. This is because the region that was targeted with the "spot-light" is associated with the receiver-stimulator position when the ventricle is full. Therefore, the QSD waveform when targeted to the QRS phase of the EKG is correlated to the left ventricle volume.

Alternatively if the "spot-light" at a phase of the cardiac cycle corresponding to an empty ventricle (end systole or early diastole, between the T and P waves), the resulting QSD waveform would be 180 degrees shifted in phase, with minimum points corresponding to a full ventricle.

Figure 8A:
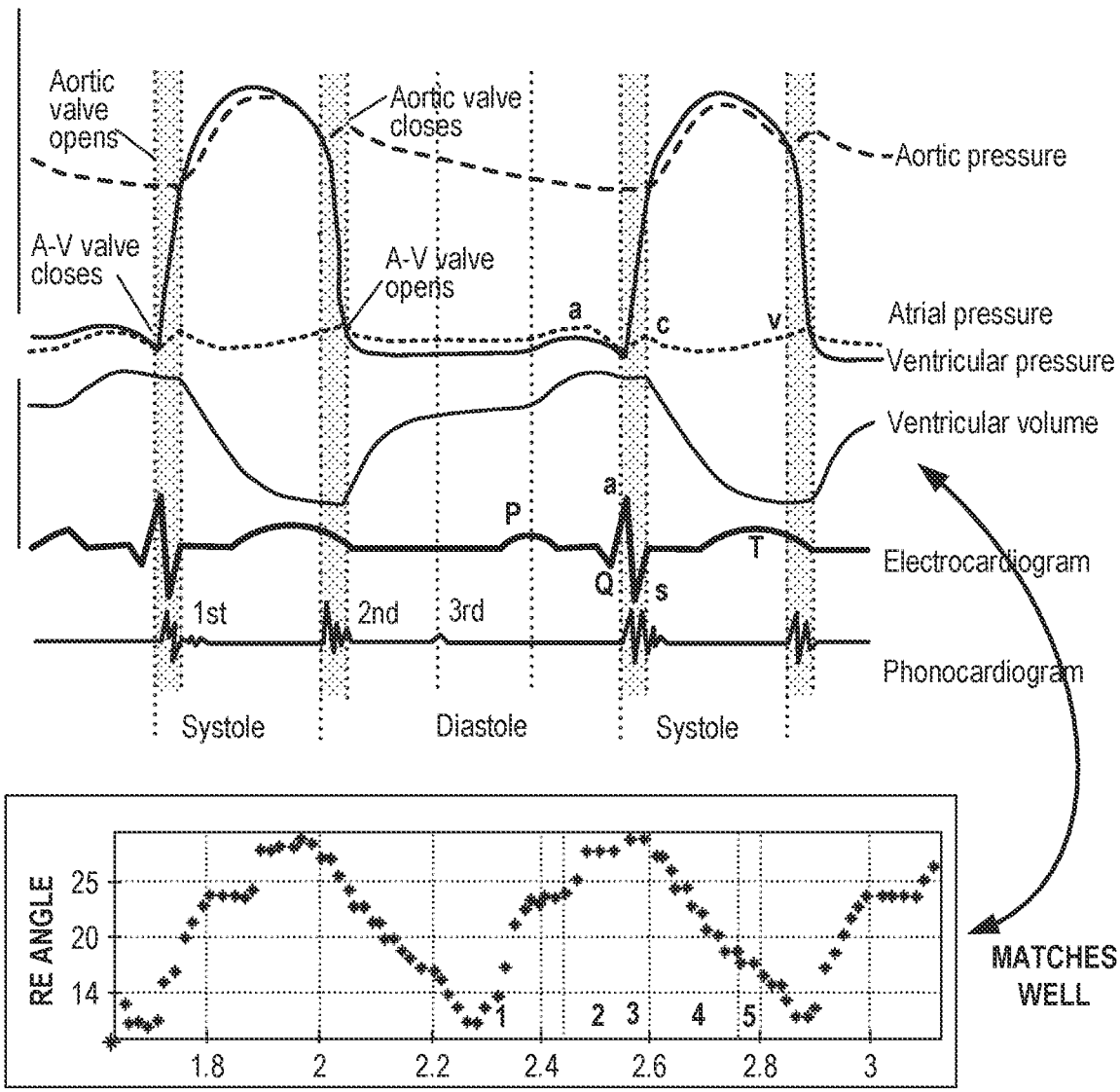
FIG. 8A-D illustrate sensor data during continuous sensing the receiver-stimulator position.
Figure 8B:
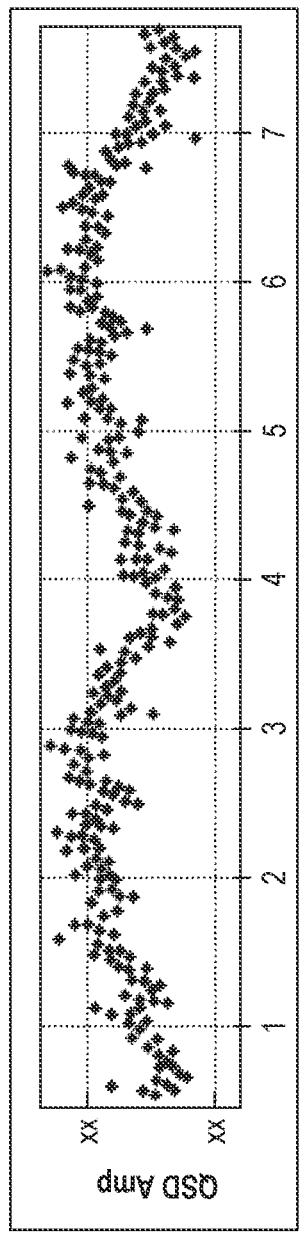
Figure 8C:
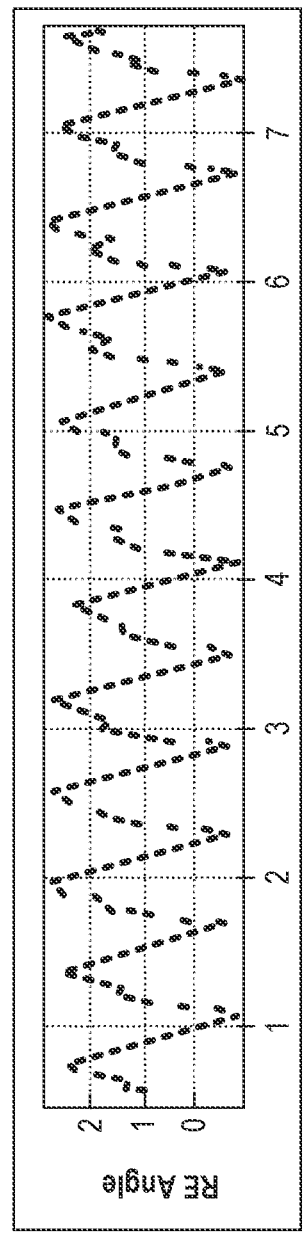
Figure 8D:
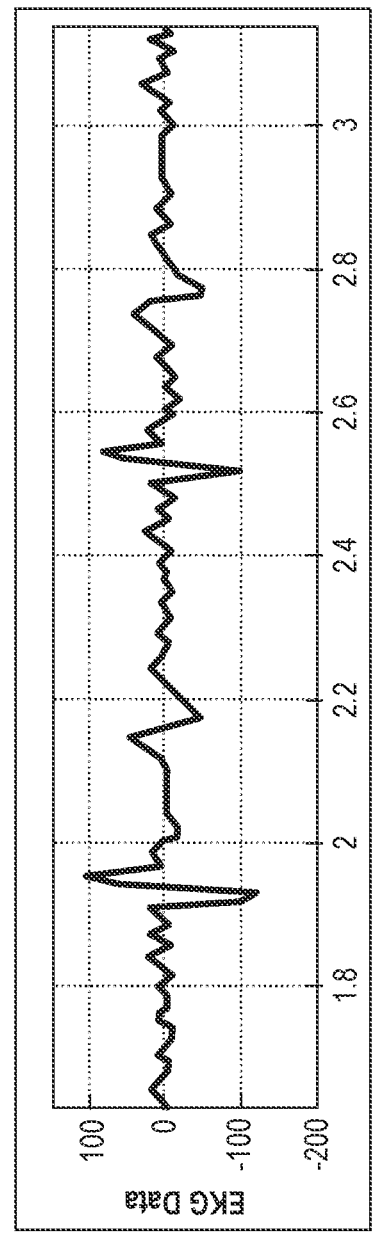
Figures 9A, 9B:
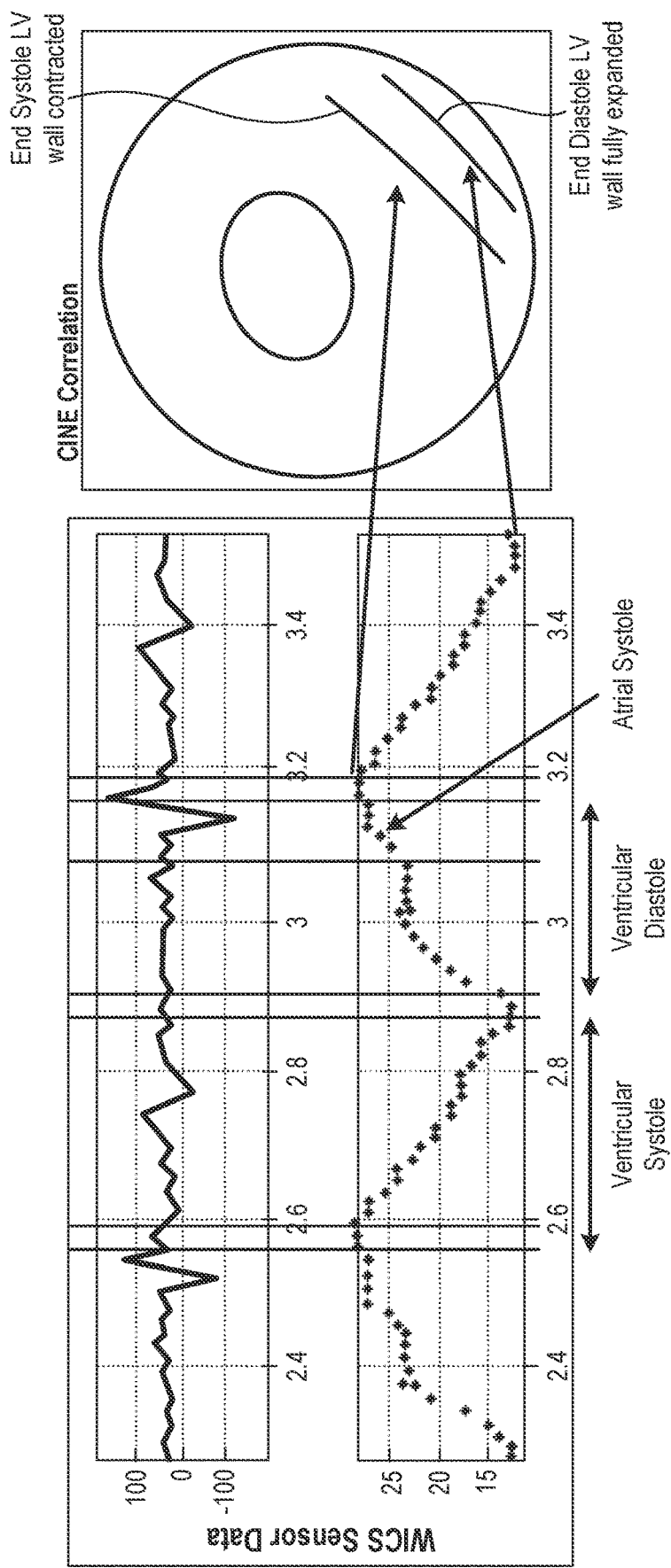
FIG. 9A-B shows a comparison of sensor data with fluoroscopic images.

In another example, continuous tracking of the receiver-stimulator location was performed every 10 ms rather than directing the spotlight to a single transmit angle. FIGS. 8A-D illustrate the receiver-stimulator position (angle and depth) as a function of cardiac cycle phase. The receiver-stimulator position shows excellent detail of the heart wall motion over the cardiac cycle, as shown in FIG. 8A, and matches well with previously published data of ventricular volume. Further, respiration is clearly evident from the data as shown in FIG. 8B-C illustrating the response amplitude from a QSD sensor overlaid with the receiver-stimulator angle. The EKG data collected from the controller-transmitter sensing electrodes show both QRS and T-waves, as shown in FIG. 8D. FIGS. 9A-9B show a comparison of controller-transmitter sensor data (FIG. 9A) with fluoroscopic images (FIG. 9B). Heart wall motion over the cardiac cycle as determined by the controller-transmitter sensor data matches with heart wall motion observed in the fluoroscopic images.

Figure 10A:
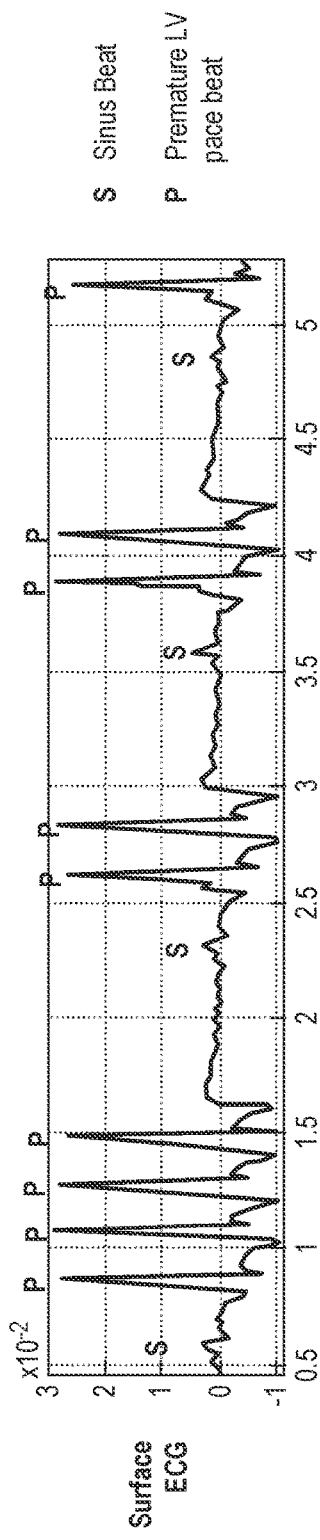
FIGS. 10A-C shows an example of abnormal hemodynamics from premature LV pacing detectable by the receiver-stimulator motion.
Figure 10B:
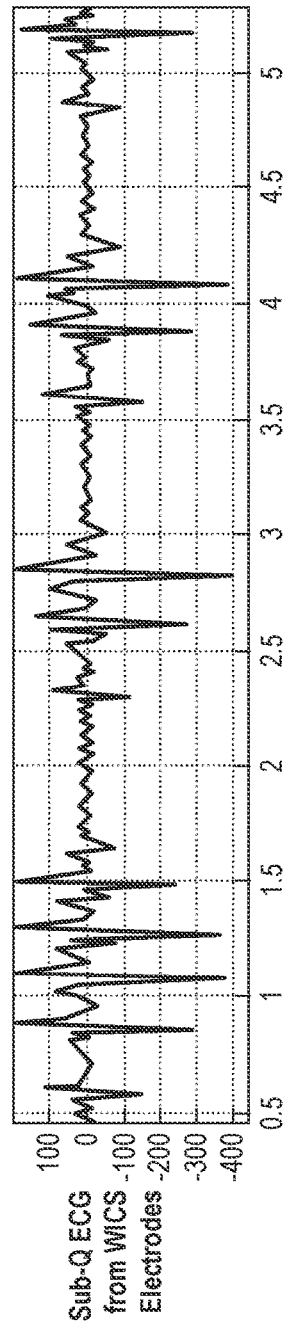
Figure 10C:
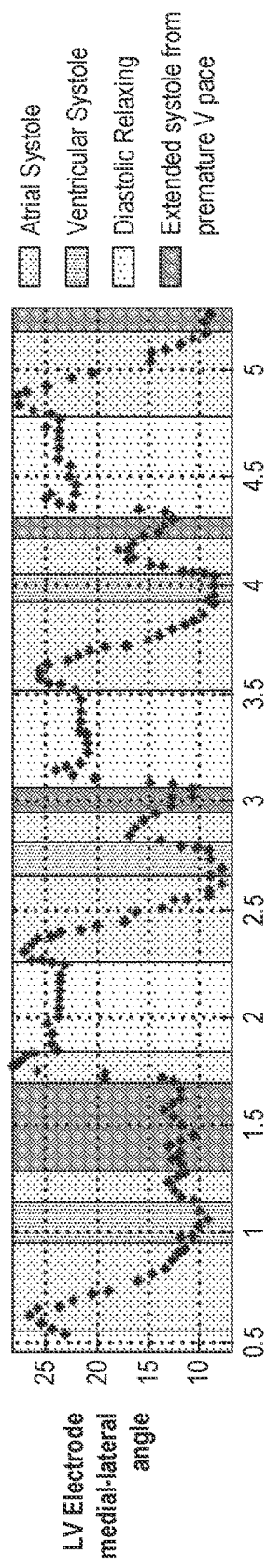

FIG. 10A-C shows an example of abnormal hemodynamics from premature LV pacing detectable by the receiver-stimulator motion. FIG. 10A shows EKG data collected using surface EKG electrodes. The hemodynamic loss or loss of motion due to rapid pacing which was not clear from electrical inputs (FIG. 10B) was clearly visible based on the receiver-stimulator motion (FIG. 10C).

Although particular embodiments have been shown and described, they are not intended to limit the invention. Various changes and modifications may be made to any of the embodiments, without departing from the spirit and scope of the invention. The invention is intended to cover alternatives, modifications, and equivalents.

What is claimed is:

1. A method for tracking and/or determining cardiac motion, comprising:
    tracking a location of an acoustic receiver-converter throughout a cardiac cycle relative to cardiac tissue;
    creating a motion profile of the receiver-converter based on the tracked location;
    using the motion profile in one or more of the following steps—
    (a) normalizing the motion profile with electrocardiogram (EKG) data,
    (b) mapping a cardiac motion of the cardiac tissue based on the motion profile, and/or
    (c) determining a magnitude of a motion of the receiver-converter through the cardiac cycle based on the motion profile and correlating the magnitude of the motion of the receiver-converter to changes in ejection fraction; and
    delivering, via the receiver-converter electrical energy to the cardiac tissue based at least in part on (a), (b), and/or (c).

2. The method of claim 1, further comprising determining a position of the receiver-converter at the end of diastole of the cardiac tissue.

3. The method of claim 2 wherein the electrical energy comprises pacing stimulation, and further comprising delivering acoustic energy to the receiver-converter sufficient to trigger the pacing stimulation of the cardiac tissue based on the determination that the receiver-converter is at the position at the end of diastole.

4. The method of claim 1 wherein tracking the location of the receiver-converter comprises detecting the electrical energy delivered by the receiver-converter to the cardiac tissue.

5. The method of claim 1 wherein the method comprises normalizing the motion profile with the EKG data.

6. The method of claim 1 wherein the method comprises mapping the cardiac motion of the cardiac tissue based on the motion profile.

7. The method of claim 1 wherein the method comprises determining the magnitude of the motion of the receiver-converter through the cardiac cycle based on the motion profile and correlating the magnitude of the motion of the receiver-converter to the changes in ejection fraction.

8. A method for tracking and/or determining cardiac motion, comprising:
    detecting electrical energy delivered by an acoustic receiver-converter to cardiac tissue throughout a cardiac cycle to dynamically track three-dimensional (3D) motion data of the receiver-converter; and
    (a) normalizing the 3D motion data with electrocardiogram (EKG) data,
    (b) mapping a location of the cardiac tissue based on the 3D motion data,
    (c) mapping the location of the cardiac tissue electromechanically by combining the 3D motion data with electrogram (EGM) data, and/or
    (d) determining a magnitude of a motion of the receiver-converter through the cardiac cycle based on the 3D motion data and correlating the magnitude of the motion of the receiver-converter to changes in ejection fraction;
    wherein the electrical energy delivered by the receiver-converter to the cardiac tissue is based at least in part on (a), (b), (c), and/or (d).

9. The method of claim 8, further comprising determining a position of the receiver-converter at the end of diastole of the cardiac tissue.

10. The method of claim 8, wherein the electrical energy comprises pacing stimulation, and further comprising delivering acoustic energy to the receiver-converter sufficient to trigger the pacing stimulation of the cardiac tissue based on the determination that the receiver-converter is at the position at the end of diastole.

11. The method of claim 8 wherein detecting the electrical energy comprises detecting the electrical energy delivered by the receiver-stimulator to the location of the cardiac tissue.

12. The method of claim 11, further comprising:
    mapping the location of the cardiac tissue electromechanically by combining the 3D motion data with the EGM data; and
    collecting the EGM data at the location of the cardiac tissue.

13. The method of claim 12 wherein collecting the EGM data comprises collecting the EGM data with the receiver-converter.

14. The method of claim 8 wherein the method comprises normalizing the 3D motion data with the EKG data.

15. The method of claim 8 wherein the method comprises mapping the location of the cardiac tissue based on the 3D motion data.

16. The method of claim 8 wherein the method comprises mapping the location of the cardiac tissue electromechanically by combining the 3D motion data with the EGM data.

17. The method of claim 8 wherein the method comprises determining the magnitude of the motion of the receiver-converter through the cardiac cycle based on the 3D motion data and correlating the magnitude of the motion of the receiver-converter to the changes in ejection fraction.

18. A method for tracking and/or determining cardiac motion, comprising:
   tracking a location of an acoustic receiver-converter throughout a cardiac cycle relative to cardiac tissue;
   creating a motion profile of the receiver-converter based on the tracked location;
   using the motion profile in one or more of the following steps—
   (a) normalizing the motion profile with electrocardiogram (EKG) data,
   (b) mapping a cardiac motion of the cardiac tissue based on the motion profile,
   (c) correlating the motion profile with electrogram (EGM) data to create an electromechanical motion profile, and/or
   (d) determining a magnitude of a motion of the receiver-converter through the cardiac cycle based on the motion profile and correlating the magnitude of the motion of the receiver-converter to changes in ejection fraction; and
   determining a position of the receiver-converter at the end of diastole of the cardiac tissue;
   and
   delivering acoustic energy to the receiver-converter sufficient to trigger pacing stimulation of the cardiac tissue based on the determination that the receiver-converter is at the position at the end of diastole.

19. The method of claim 18 wherein the method further comprises:
   correlating the motion profile with the EGM data to create the electromechanical motion profile; and
   collecting the EGM data with the receiver-converter at the location of the cardiac tissue.

20. The method of claim 18 wherein the method comprises correlating the motion profile with the EGM data to create the electromechanical motion profile.

21. A system for tracking and/or determining cardiac motion, comprising:
   a processing element; and
   a non-transitory computer-readable storage element storing instructions that, when executed by the processing element, cause a tissue stimulation system to perform operations comprising—
   tracking a location of an acoustic receiver-converter throughout a cardiac cycle relative to cardiac tissue;
   creating a motion profile of the receiver-converter based on the tracked location; and
   using the motion profile in one or more of the following steps—
   (a) normalizing the motion profile with electrocardiogram (EKG) data,
   (b) mapping a cardiac motion of the cardiac tissue based on the motion profile, and/or
   (c) determining a magnitude of a motion of the receiver-converter through the cardiac cycle based on the motion profile and correlating the magnitude of the motion of the receiver-converter to changes in ejection fraction; and
   delivering, via the receiver-converter, electrical energy to the cardiac tissue based at least in part on (a), (b), and/or (c).

22. A system for tracking and/or determining cardiac motion, comprising:
   a processing element; and
   a non-transitory computer-readable storage element storing instructions that, when executed by the processing element, cause a tissue stimulation system to perform operations comprising—
   detecting electrical energy delivered by an acoustic receiver-converter to cardiac tissue throughout a cardiac cycle to dynamically track three-dimensional (3D) motion data of the receiver-converter; and
   using the 3D motion data in one or more of the following steps—
   (a) normalizing the 3D motion data with electrocardiogram (EKG) data,
   (b) mapping a location of the cardiac tissue based on the 3D motion data,
   (c) mapping the location of the cardiac tissue electromechanically by combining the 3D motion data with electrogram (EGM) data, and/or
   (d) determining a magnitude of a motion of the receiver-converter through the cardiac cycle based on the 3D motion data and correlating the magnitude of the motion of the receiver-converter to changes in ejection fraction;
   wherein the electrical energy delivered by the receive-converter to the cardiac tissue is based at least in part on (a), (b), (c), and/or (d).

23. A method for tracking and/or determining cardiac motion, comprising:
   tracking a location of an acoustic receiver-converter throughout a cardiac cycle relative to cardiac tissue by detecting electrical energy delivered by the receiver-converter to the cardiac tissue;
   creating a motion profile of the receiver-converter based on the tracked location; and
   using the motion profile in one or more of the following steps—
   (a) normalizing the motion profile with electrocardiogram (EKG) data,
   (b) mapping a cardiac motion of the cardiac tissue based on the motion profile,
   (c) correlating the motion profile with electrogram (EGM) data to create an electromechanical motion profile, and/or
   (d) determining a magnitude of a motion of the receiver-converter through the cardiac cycle based on the motion profile and correlating the magnitude of the motion of the receiver-converter to changes in ejection fraction;
   wherein the electrical energy delivered by the receiver-converter to the cardiac tissue is based at least in part on (a), (b), (c), and/or (d).

* * * * *